US 11,839,742 B2

(12) United States Patent
Willybiro et al.

(10) Patent No.: US 11,839,742 B2
(45) Date of Patent: Dec. 12, 2023

(54) INTRAVENOUS DEVICE WITH INTEGRATED SENSORS

(71) Applicant: Becton, Dickinson and Company, Franklin Lakes, NJ (US)

(72) Inventors: Kathryn Willybiro, Park City, UT (US); Jonathan Karl Burkholz, Salt Lake City, UT (US); Joseph Spataro, Cottonwood Heights, UT (US); Yiping Ma, Layton, UT (US); Huy Tran, Riverton, UT (US); Bart D. Peterson, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 793 days.

(21) Appl. No.: 16/743,696

(22) Filed: Jan. 15, 2020

(65) Prior Publication Data
US 2020/0230320 A1 Jul. 23, 2020

Related U.S. Application Data (60) Provisional application No. 62/794,433, filed on Jan. 18, 2019.

(51) Int. Cl.
*A61M 5/172* (2006.01)
*A61M 25/02* (2006.01)
*A61M 25/06* (2006.01)

(52) U.S. Cl.
CPC .......... *A61M 5/1723* (2013.01); *A61M 25/02* (2013.01); *A61M 25/0606* (2013.01); *A61M 2005/1726* (2013.01); *A61M 2025/0266* (2013.01); *A61M 2205/3303* (2013.01); *A61M 2205/3306* (2013.01); *A61M 2205/3327* (2013.01); *A61M 2205/3561* (2013.01); *A61M 2205/3584* (2013.01); *A61M 2205/50* (2013.01); *A61M 2207/00* (2013.01); *A61M 2230/20* (2013.01); *A61M 2230/30* (2013.01); *A61M 2230/50* (2013.01); *A61M 2230/63* (2013.01)

(58) Field of Classification Search
CPC ................ A61M 5/1723; A61M 25/02; A61M 25/0606; A61M 2005/1726; A61M 2025/0266; A61M 2205/3303; A61M 2205/3306; A61M 2205/3327
USPC .......................................... 604/66
See application file for complete search history.

(56) References Cited

U.S. PATENT DOCUMENTS

2004/0193025 A1   9/2004   Steil et al.
2004/0204689 A1  10/2004   Lynn
2017/0086746 A1*  3/2017   Ofek ...................... A61B 5/283

FOREIGN PATENT DOCUMENTS

JP   2008541799 A   11/2008
JP   2018061836 A    4/2018
JP   2018531674 A   11/2018
WO   2018125845 A1   7/2018

(Continued)

*Primary Examiner* — Phillip A Gray
(74) *Attorney, Agent, or Firm* — Kirton McConkie; Whitney Blair; Kevin Stinger (57) ABSTRACT

An intravenous (IV) device, may include a needle; a catheter coaxially formed around the needle; a fluidic path fluidically coupled to a hollow formed through the needle and catheter; and a printed circuit board (PCB), including: a network interface device; a plurality of sensors operatively coupled to the fluidic path to measure a biological characteristic related to a plurality of patient vitals.

20 Claims, 5 Drawing Sheets

(56) References Cited

FOREIGN PATENT DOCUMENTS

WO      2018204668 A1   11/2018
WO      2019/228991     12/2019

\* cited by examiner

INTRAVENOUS DEVICE WITH INTEGRATED SENSORS

RELATED APPLICATIONS

This application claims the benefit of U.S. Provisional Application No. 62/794,433, filed Jan. 18, 2019, and entitled AUGMENTED INFUSION UTILIZING CATHETER-BASED PATIENT MONITORING, which is incorporated herein in its entirety.

BACKGROUND

Some intravenous therapy systems include and intravenous (IV) device that includes a needle and catheter axially formed around the needle with any tubing fluidically coupling the IV device to other devices associated with the IV device. The IV device may be used for a variety of infusion therapies. For example, the IV device may be used for infusing fluids, such as a saline solution, various medicaments, and parenteral nutrition, into a patient. The IV device may also be used for withdrawing blood from the patient. To facilitate insertion into a body, the needle of the intravenous therapy system includes a distal tip that includes a bevel used to interface with a skin of a patient as the bevel faces away from skin of the patient.

The subject matter claimed herein is not limited to embodiments that solve any disadvantages or that operate only in environments such as those described herein. Rather, this background is provided to describe an environment in which the presently described embodiments may operate.

SUMMARY

The present disclosure relates generally to an intravenous device that utilizes a plurality of integrated sensors to provide continuous and real-time measurements of various patient vitals. In an embodiment, an intravenous (IV) device includes a needle; a catheter coaxially formed around the needle; a fluidic path fluidically coupled to a hollow formed through the needle and catheter; and a printed circuit board (PCB), that includes a network interface device and a plurality of sensors operatively coupled to the fluidic path to measure a biological characteristic related to a plurality of patient vitals. In an embodiment, the plurality of sensors includes a pressure sensor fluidically coupled to a fluid path in the IV device to measure a pulse of the patient. In an embodiment, the plurality of sensors includes a temperature sensor to measure a temperature of blood within the patient's body. In an embodiment, the plurality of sensors includes an optical sensor to measure an oxygen level within blood of the patient's body. In an embodiment, the includes an accelerometer to detect a rapid fall of the patient when the intravenous therapy system is inserted into the patient's body.

With the sensors placed directly integral with the intravenous device, the intravenous device may serve as a central hub located centrally and accessible by a clinician, either by a wireless or wired connection, from a computing device communicatively coupled to the intravenous device. There may be many scenarios when continuous patient monitoring would result in prompt care that saves time, money, and the health and safety of the patient. By way of example, such monitoring provided by the use of the presently-described intravenous device may alert a clinician to potential adverse patient reactions to toxic drugs often used for chemotherapy. In any patient-monitoring scenarios, the presently-described intravenous device would eliminate a potential trip to the emergency room by an emergency medical technician.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

As used herein, the term "proximal" refers to a location on the needle of an intravenous therapy system that, during use, is closest to the clinician using the intravenous therapy system and farthest from the patient in connection with whom the device is used. Conversely, the term "distal" refers to a location on the needle of an intravenous therapy system that, during use, is farthest from the clinician using the intravenous therapy system and closest to the patient in connection with whom the intravenous therapy system is used.

As used herein, the term "top", "up" or "upwardly" refers to a location on the needle of this intravenous therapy system that, during use, is radially away from the longitudinal axis of the intravenous therapy system and away from the patient's skin. Conversely, as used herein, the term "bottom", "down" or "downwardly" refers to a location on the needle of this intravenous therapy system that, during use, is radially away from the longitudinal axis of the device and toward the patient's skin.

As used herein, the term "in" or "inwardly" refers to a location with respect to the needle of this intravenous therapy system that, during use, is toward the inside of the intravenous therapy system. Conversely, as used herein, the term "out" or "outwardly" refers to a location with respect to the needle of this intravenous therapy system that, during use, is toward the outside of the intravenous therapy system.

As used herein, the term "formed" refers to the construction, creation, production, arrangement, or placement of an element.

This invention is described herein using like reference numbers for like elements in the different embodiments.

Although the embodiments described herein are used in connection for use as an intravenous therapy system to receive a blood sample or introduce a medicament into the body of a patient, it is to be understood that this intravenous therapy system is applicable to other medical devices where it is desirable for a needle and/or catheter to be inserted into a blood vessel of a patient. In addition, while the embodiments of the intravenous therapy system are satisfied by embodiments in many different forms, there are shown in the drawings and herein described in detail, preferred embodiments of the invention with the scope of the disclosure measured by the appended claims.

Figure 1:
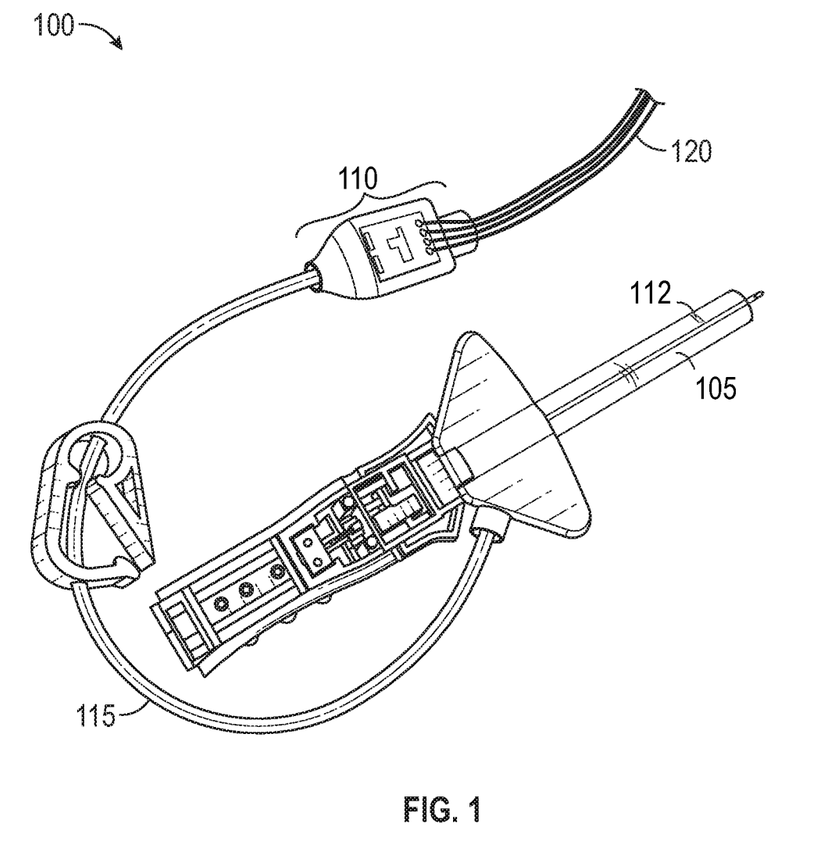
FIG. 1 is a perspective view of an intravenous device according to an embodiment of the present disclosure.

FIG. 1 is a perspective view of an intravenous device 100 according to an embodiment of the present disclosure. The intravenous device 100 described herein may include any type of device that may be fluidically coupled to a patient's bloodstream at a blood vessel. In an embodiment, the intravenous device 100 may include a needle and catheter 105 that is used by a clinician or other health care provider (HCP) to access the patient's blood vessel. The clinician may introduce the needle and catheter 105 into the patient's body at a location where the needle and catheter may intersect with a blood vessel within the patient's body. In some embodiments, the needle may extend through the catheter 105.

In an embodiment, the intravenous device 100 may include a fluidic path formed within the hollow of the needle and catheter that fluidically couples to a section of tubing 115. The tubing 115, in an embodiment, may be clear so as to allow a clinician to see fluids that may enter the tubing 115 during, for example, a blood draw or an infusion of one or more infusing fluids, such as normal saline solution, various medicaments, and total parenteral nutrition. In an embodiment, the tubing 115 may include any type of clamping device to alter the flow of these fluids through the tubing 115.

In the embodiments presented herein, the intravenous device 100 may include a printed circuit board (PCB) 110. In the embodiment shown in FIG. 1, the PCB 110 may be integrated into a part of the intravenous device 100 at or on a part of the intravenous device 100 such as the tubing 115. In an embodiment, the PCB 110 may be communicatively coupled to any type of sensor 112 that is used to measure a biological characteristic related to a plurality of patient vitals. In an embodiment, these sensors 112 may be communicatively coupled to the PCB 110, physically coupled to the PCB 110, or both communicatively and physically coupled to the PCB 110.

In an embodiment, the PCB 110 may be physically or communicatively coupled to a pressure sensor. In an embodiment, the pressure sensor may measure a pressure of fluids passed through the tubing 115, adaptor, connector, or other fluidic channel formed in the intravenous device 100. In an embodiment, the PCB 110 may be placed such that the pressure sensor is also in fluidic communication with the tubing 115 or other fluidic channel. In an embodiment, the pressure sensor may measure the pulse of the of the patient. In this embodiment, the pressure sensor may be placed along a fluidic path through which blood may pass during, for example, a blood drawing procedure.

In an embodiment, the pressure sensor is coupled to a processor. The processor may receive data from the pressure sensor descriptive of pressures within the blood vessel the intravenous device 100 is inserted into and, therefore, fluidically coupled to. In an embodiment, the processor may execute a fast Fourier transform that detects a pressure trace indicating a pulse rate of the patient. Other types of processes or algorithms may be used to determine a pulse rate of the patient after receiving the data from the pressure sensor.

In an embodiment, the PCB 110 may be physically or communicatively coupled to an optical sensor. In an embodiment, the optical sensor may detect a level of oxygen within the patient's blood (e.g., either at a vein or artery). In this embodiment, the optical sensor may include a camera that detects infrared (IR) or near-IR light. The light absorbed by the camera is a function of the oxygenation of the hemoglobin within the patient's blood. In an embodiment, the optical sensor may also include an IR diode or other IR light emitting device that allows IR light to be reflected off of the patient's blood and detected by the IR camera. The optical sensor may, in an embodiment, be a pulse oximeter that measures an oxygen saturation of the blood within the patient's body by recording an amount go light transmitted or reflected by deoxygenated versus oxygenated hemoglobin as detected during a pulse of blood within the patient's body.

In an embodiment, the optical sensor may be used to detect the pulse of the patient. In this embodiment, a light-emitting diode (LED) or other light source may be used according to the principles of plethysmography. As a change a volume of blood through an organ, such as the skin of the patient, may cause a change in light intensity through or reflected through the skin such that the optical sensor may detect such changes indicating a pulse. The results from the optical sensor indicating a pulse rate may be compared, in an embodiment, to a detected pulse rate detected by the pressure sensor described herein. This comparison may be conducted by the processor so as to determine an average of the pulse detected.

In an embodiment, the optical sensor may be placed within or near the tubing 115 of the intravenous device 100. In an embodiment, the optical sensor may be placed at any location where a sample of the patient's blood may be optically accessed by the optical sensor in order to detect the oxygenation of patient's blood. In an embodiment, the optical sensor may form part of the stabilization patch described herein. In any of these embodiments, the optical sensor may be communicatively coupled to the processor in order to provide to the processor data descriptive of the pulse of the patient and/or the oxygenation of the patient's blood.

In an embodiment, the PCB 110 may be physically or communicatively coupled to temperature sensor. The temperature sensor may measure the temperature of the blood within the patient's body. The temperature sensor, in an embodiment, may be placed within the tubing 115 of the intravenous device 100. In an embodiment, the temperature sensor may be placed on an outer surface of the tubing 115. In an embodiment, the temperature sensor may be in fluidic contact with venous blood such that the temperature of the blood within the patient's blood may be measured.

In an embodiment, the PCB 110 may be physically or communicatively coupled to an accelerometer. The accelerometer may be nay device that measures the movement of the intravenous device 100. The accelerometer, in an embodiment, may measure the proper acceleration of the intravenous device 100: that being the acceleration of the intravenous device 100 in its own instantaneous rest frame. The accelerometer may detect, in an example, a fall experience by a patient. This fall indicator in the form of the accelerometer may allow a clinician to detect, in real-time, a potential fall incident of the patient in order to render aid to the patient as soon as possible.

Figure 4:
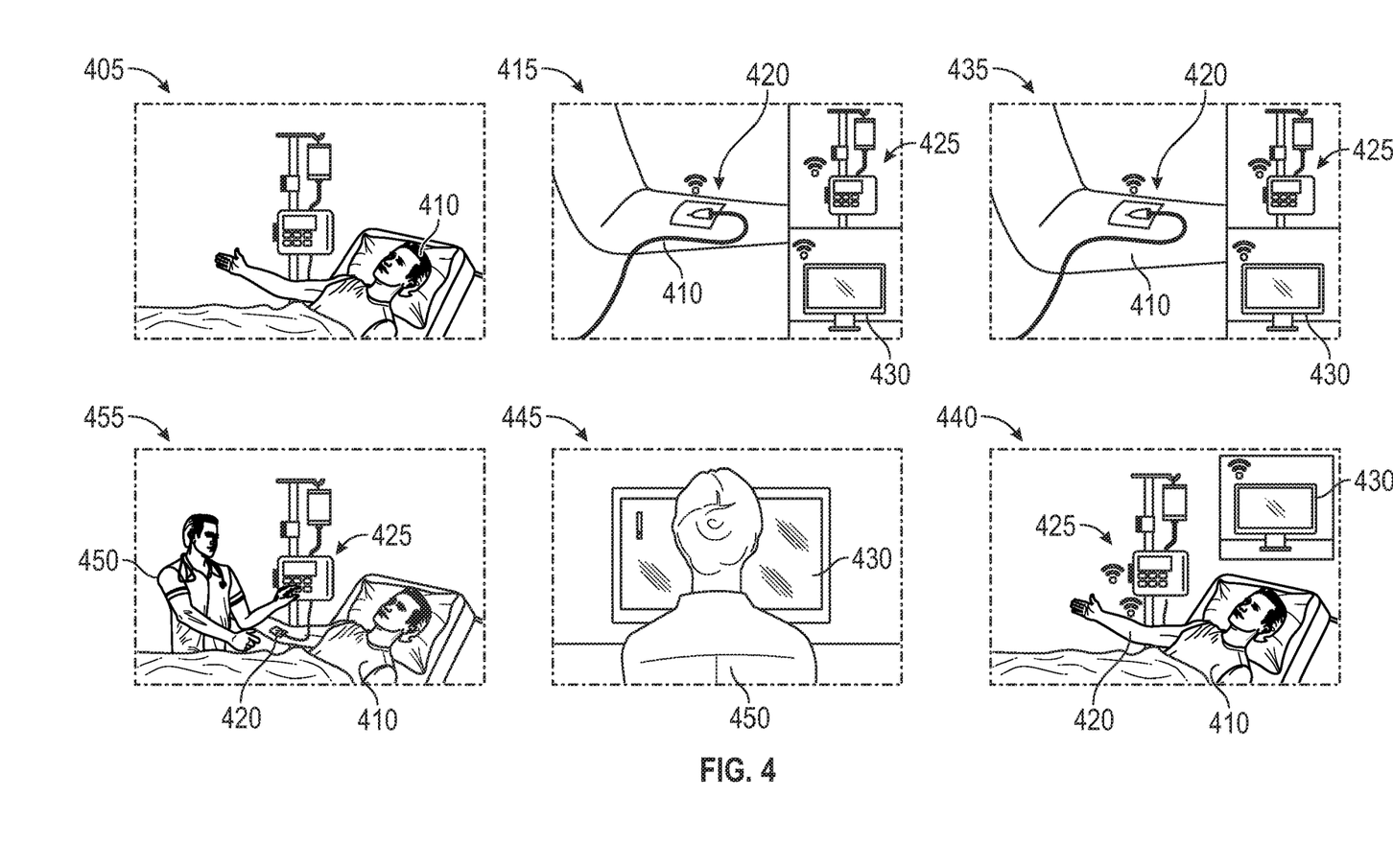
FIG. 4 is a flow diagram illustrating a method of operating an intravenous therapy system according to an embodiment of the present disclosure.

In an embodiment, the pressure sensor, the temperature sensor, the optical sensor, and the accelerometer may be communicatively coupled to a processor. The processor may be formed on any part of the intravenous device 100 or may be remote from the intravenous device 100. In the embodiments where the processor forms part of the intravenous device 100, the processor may be formed on the PCB 110 and communicatively coupled to each of the sensors as described herein. In the embodiment where the processor is placed remote of the intravenous device 100, the processor may be included within a computing device communicatively coupled to the sensors of the PCB 110 via a network interface device formed on the intravenous device 100. In the embodiment where the processor is placed remote of the intravenous device 100, the processor may form part of a stabilization patch used to secure the intravenous device 100 to the patient's body when the intravenous device 100 has interfaced with the patient's blood vessel. In this embodiment, the stabilization patch may also include a network interface device that communicatively couples the processor to a computing device, the PCB 110 of the intravenous device 100, or both. An example of a stabilization patch that is secured overtop an intravenous device to secure the intravenous device to the patient's body is shown in FIG. 4.

Although the present specification described specific sensors coupled to the intravenous device 100 or a stabilization patch, these sensors are meant to be example sensors that may be used to detect a biological characteristic related to a plurality of patient vitals. However, the present specification contemplates that other types of sensors may be physically coupled to the intravenous device 100 or stabilization patch. The present description contemplates that these other types of sensors may be used without going beyond the scope of the principles described herein.

In any embodiment described herein, the sensors may be in the form of a microfluidic chip. The microfluidic chip may reduce the sizes of the sensors that may be on the order of microliters, nanoliters, picoliters, and femtoliters. The devices within the microfluidic chip may be placed along microfluidic channels formed therein.

FIG. 1 further illustrates a number of electrical lines 120 communicatively coupled to the PCB 110. These electrical lines 120 may be used to communicatively couple the PCB 110 and its associated sensors and network interface device with, for example, a computing device, a power source, or both.

The intravenous device 100 may further be operatively coupled to a power source (not shown) such as a battery or AC power source. In an embodiment, a battery may be formed on the PCB 110 to power the various sensors thereof. The battery may provide power to these sensors so that the intravenous device 100 may be continually operated during the useful life of the intravenous device 100. In some examples, the useful life of an intravenous device 100 may be as long as 30 days or more.

Figure 2:
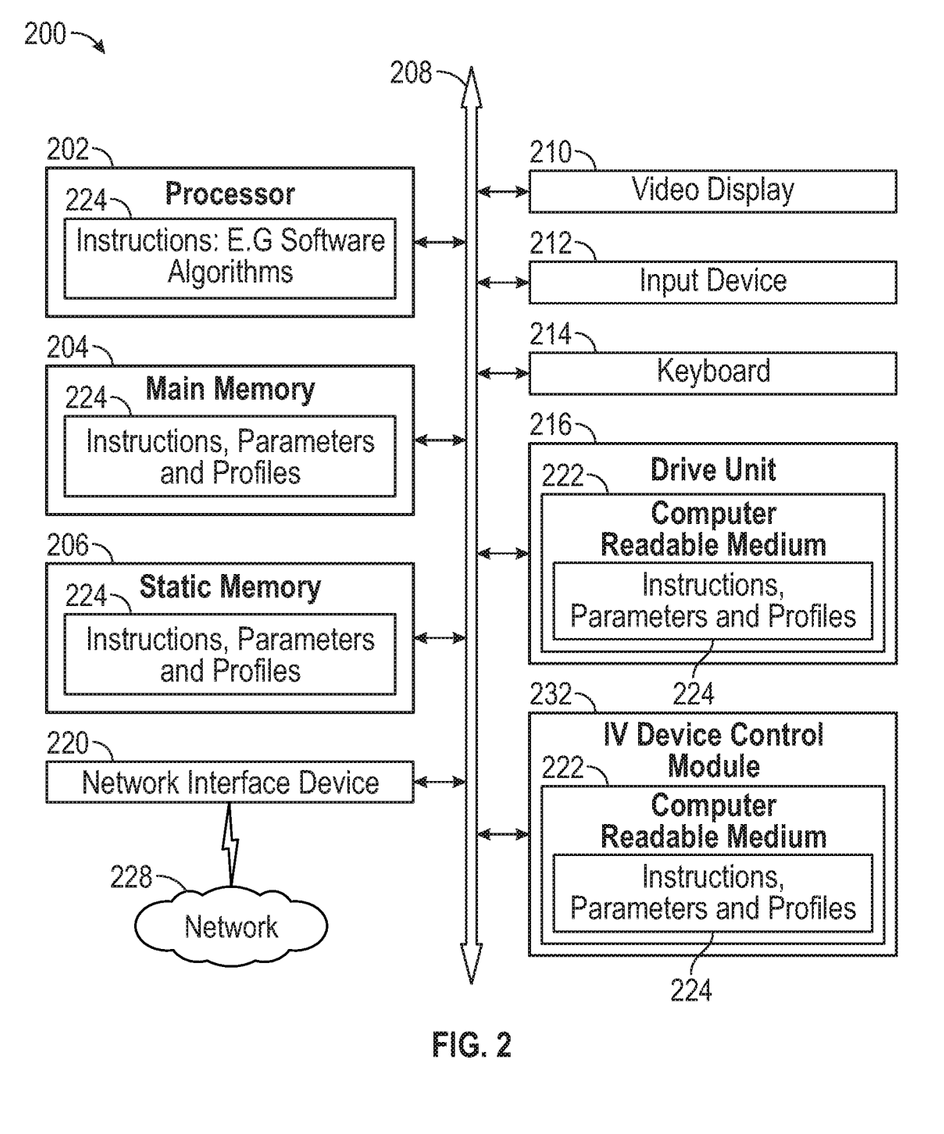
FIG. 2 is a block diagram of an intravenous system according to an embodiment of the present disclosure.

FIG. 2 is a block diagram of an intravenous system 200 according to an embodiment of the present disclosure. In the embodiments described herein, an intravenous system 200 may include a computing device that includes any instrumentality or aggregate of instrumentalities operable to compute, classify, process, transmit, receive, retrieve, originate, switch, store, display, manifest, detect, record, reproduce, handle, or use any form of information, intelligence, or data for business, scientific, control, entertainment, or other purposes. For example, a computing device present in the intravenous system 200 may include a personal computer, mobile device (e.g., personal digital assistant (PDA) or smart phone), server (e.g., blade server or rack server), a consumer electronic device, a network server or storage device, a network router, switch, or bridge, wireless router, or other network communication device, a network connected device (cellular telephone, tablet device, etc.), IoT computing device, wearable computing device, a set-top box (STB), a mobile computing device, a palmtop computer, a laptop computer, a desktop computer, a communications device, an access point (AP), a base station transceiver, a wireless telephone, a control system, a camera, a printer, a pager, a personal trusted device, a web appliance, or any other suitable machine capable of executing a set of instructions (sequential or otherwise) that specify actions to be taken by that machine, and may vary in size, shape, performance, price, and functionality.

In a networked deployment, the computing device of the intravenous system 200 may operate in the capacity of a server or as a client computer in a server-client network environment, or as a peer computer system in a peer-to-peer (or distributed) network environment. In a particular embodiment, the computing device may be implemented using electronic devices that provide voice, video or data communication. For example, a computing device may be any mobile or other computing device capable of executing a set of instructions (sequential or otherwise) that specify actions to be taken by that machine. Further, while a single computing device 200 is illustrated, the term "system" shall also be taken to include any collection of systems or sub-systems that individually or jointly execute a set, or multiple sets, of instructions to perform one or more computer functions. In some embodiments, the intravenous system 200 may include a computing device that is operatively coupled to the intravenous device described in connection with FIG. 1. In this example, the computing device may include those processing, video, input, and memory resources used in connection with the intravenous device.

The computing device may include memory (volatile (e.g. random-access memory, etc.), nonvolatile (read-only memory, flash memory etc.) or any combination thereof), one or more processing resources, such as a central processing unit (CPU), a graphics processing unit (GPU), hardware or software control logic, or any combination thereof. Additional components of the computing device may include one or more storage devices, one or more communications ports for communicating with external devices, as well as, various input and output (I/O) devices, such as a keyboard, a mouse, a video/graphic display, or any combination thereof. The computing device may also include one or more buses operable to transmit communications between the various hardware components. Portions of a computing device may themselves be considered computing devices.

The computing device may include devices or modules that embody one or more of the devices or execute instructions for the one or more systems and modules described herein, and operates to perform one or more of the methods described herein. The computing device may execute code instructions 224 that may operate on servers or systems, remote data centers, or on-box in individual client computing devices according to various embodiments herein. In some embodiments, it is understood any or all portions of code instructions 224 may operate on a plurality of computing devices that are each operatively coupled to the intravenous device.

The computing device may include a processor 202 such as a central processing unit (CPU), control logic or some combination of the same. Any of the processing resources may operate to execute code that is either firmware or software code. Moreover, the computing device may include memory such as main memory 204, static memory 206, computer readable medium 222 storing instructions 224 of the comparator 232, and drive unit 216 (volatile (e.g. random-access memory, etc.), nonvolatile (read-only memory, flash memory etc.) or any combination thereof). The computing device may also include one or more buses 208 operable to transmit communications between the various hardware components such as any combination of various input and output (I/O) devices.

The computing device may further include a video display 210. The video display 210 in an embodiment may function as a liquid crystal display (LCD), an organic light emitting diode (OLED), a flat panel display, a solid-state display, or a cathode ray tube (CRT). Additionally, the computing device may include an input device 212, such as a cursor control device (e.g., mouse, touchpad, or gesture or touch screen input, and a keyboard 214.

The network interface device 220 may provide connectivity to a network 228, e.g., a wide area network (WAN), a local area network (LAN), wireless local area network (WLAN), a wireless personal area network (WPAN), a wireless wide area network (WWAN), or other networks. Connectivity may be via wired or wireless connection. The network interface adapter 220 may operate in accordance with any wireless data communication standards. To communicate with a wireless local area network, standards including IEEE 802.11 WLAN standards, IEEE 802.15 WPAN standards, WWAN such as 3GPP or 3GPP2, or similar wireless standards may be used. In some aspects of the present disclosure, one network interface adapter 220 may operate two or more wireless links. In the embodiments described herein, the network interface adapter 220 may wirelessly couple the computing device with a plurality of sensors of the intravenous device described herein in order to receive an process data from those sensors and provide information and warnings to a clinician or other HCP relating to biological characteristics related to a plurality of patient vitals.

In some embodiments, software, firmware, dedicated hardware implementations such as application specific integrated circuits, programmable logic arrays and other hardware devices may be constructed to implement one or more of some systems and methods described herein. Applications that may include the apparatus and systems of various embodiments may broadly include a variety of electronic and computer systems. One or more embodiments described herein may implement functions using two or more specific interconnected hardware modules or devices with related control and data signals that may be communicated between and through the modules, or as portions of an application-specific integrated circuit. Accordingly, the present system encompasses software, firmware, and hardware implementations.

In accordance with various embodiments of the present disclosure, the methods described herein may be implemented by firmware or software programs executable by a controller or a processor system. Further, in an exemplary, non-limited embodiment, implementations may include distributed processing, component/object distributed processing, and parallel processing. Alternatively, virtual computer system processing may be constructed to implement one or more of the methods or functionalities as described herein.

The present disclosure contemplates a computer-readable medium that includes instructions, parameters, and profiles 224 or receives and executes instructions, parameters, and profiles 224 responsive to a propagated signal, so that a device connected to a network 228 may communicate voice, video or data over the network 228. Further, the instructions 224 may be transmitted or received over the network 228 via the network interface device or wireless adapter 220.

The computing device may include a set of instructions 224 that may be executed to cause the computer system to perform any one or more of the methods or computer-based functions disclosed herein. For example, instructions 224 may execute an intravenous (IV) device control module 232, software agents, or other aspects or components. Various software modules comprising application instructions 224 may be coordinated by an operating system (OS), and/or via an application programming interface (API). An example operating system may include Windows®, Android®, and other OS types. Example APIs may include Win 32, Core Java API, or Android APIs.

The disk drive unit 216 and the IV device control module 232 may include a computer-readable medium 222 in which one or more sets of instructions 224 such as software may be embedded. Similarly, main memory 204 and static memory 206 may also contain a computer-readable medium for storage of one or more sets of instructions, parameters, or profiles 224. The disk drive unit 216 and static memory 206 may also contain space for data storage. Further, the instructions 224 may embody one or more of the methods or logic as described herein. For example, instructions relating to processing of optical sensor data, accelerometer data, temperature sensor data, pressure sensor data, software algorithms, processes, and/or methods may be stored here. In a particular embodiment, the instructions, parameters, and profiles 224 may reside completely, or at least partially, within the main memory 204, the static memory 206, and/or within the disk drive 216 during execution by the processor 202 of computing device. As explained, some or all of the IV device control module 232 may be executed locally or remotely. The main memory 204 and the processor 202 also may include computer-readable media.

Main memory 204 may contain computer-readable medium (not shown), such as RAM in an example embodiment. An example of main memory 204 includes random access memory (RAM) such as static RAM (SRAM), dynamic RAM (DRAM), non-volatile RAM (NV-RAM), or the like, read only memory (ROM), another type of memory, or a combination thereof. Static memory 206 may contain computer-readable medium (not shown), such as NOR or NAND flash memory in some example embodiments. The comparator 232 may be stored in static memory 206, or the drive unit 216 on a computer-readable medium 222 such as a flash memory or magnetic disk in an example embodiment. While the computer-readable medium is shown to be a single medium, the term "computer-readable medium" includes a single-medium or multiple medium, such as a centralized or distributed database, and/or associated caches and servers that store one or more sets of instructions. The term "computer-readable medium" shall also include any medium that is capable of storing, encoding, or carrying a set of instructions for execution by a processor or that cause a computer system to perform any one or more of the methods or operations disclosed herein.

In a particular non-limiting, exemplary embodiment, the computer-readable medium may include a solid-state memory such as a memory card or other package that houses one or more non-volatile read-only memories. Further, the computer-readable medium may be a random-access memory or other volatile re-writable memory. Additionally, the computer-readable medium may include a magneto-optical or optical medium, such as a disk or tapes or other storage device to store information received via carrier wave signals such as a signal communicated over a transmission medium. Furthermore, a computer readable medium may store information received from distributed network resources such as from a cloud-based environment. A digital file attachment to an e-mail or other self-contained information archive or set of archives may be considered a distribution medium that is equivalent to a tangible storage medium. Accordingly, the disclosure is considered to include any one or more of a computer-readable medium or a distribution medium and other equivalents and successor media, in which data or instructions may be stored.

The computing device may also include the IV device control module 232 that may be operably connected to the bus 208. The computer readable medium 222 of the IV device control modules 232 may also contain space for data storage. The IV device control module 232 may, according to the present description, perform tasks related to receiving data descriptive of a pulse rate of a patient, blood temperature, blood oxygen level, and fall detection that is used to provide information and warnings to a clinician or other HCP.

In an embodiment, the IV device control module 232 may communicate with the main memory 204, the processor 202, the video display 210, the input device 212, and the network interface device 220 via bus 208, and several forms of communication may be used, including ACPI, SMBus, a 24 MHZ BFSK-coded transmission channel, or shared memory. Keyboard driver software, firmware, controllers and the like may communicate with applications on the computing device.

In other embodiments, dedicated hardware implementations such as application specific integrated circuits, programmable logic arrays and other hardware devices may be constructed to implement one or more of the methods described herein. Applications that may include the apparatus and systems of various embodiments may broadly include a variety of electronic and computer systems. One or more embodiments described herein may implement functions using two or more specific interconnected hardware modules or devices with related control and data signals that may be communicated between and through the modules, or as portions of an application-specific integrated circuit. Accordingly, the present system encompasses software, firmware, and hardware implementations.

When referred to as a "system", a "device," a "module," a "controller," or the like, the embodiments described herein may be configured as hardware. For example, a portion of an computing device may be hardware such as, for example, an integrated circuit (such as an Application Specific Integrated Circuit (ASIC), a Field Programmable Gate Array (FPGA), a structured ASIC, or a device embedded on a larger chip), a card (such as a Peripheral Component Interface (PCI) card, a PCI-express card, a Personal Computer Memory Card International Association (PCMCIA) card, or other such expansion card), or a system (such as a motherboard, a system-on-a-chip (SoC), or a stand-alone device). The system, device, controller, or module may include software, including firmware embedded at a device, such as an Intel® Core class processor, ARM® brand processors, Qualcomm® Snapdragon processors, or other processors and chipsets, or other such device, or software capable of operating a relevant environment of the computing device. The system, device, controller, or module may also include a combination of the foregoing examples of hardware or software. In an embodiment a computing device may include an integrated circuit or a board-level product having portions thereof that may also be any combination of hardware and software. Devices, modules, resources, controllers, or programs that are in communication with one another need not be in continuous communication with each other, unless expressly specified otherwise. In addition, devices, modules, resources, controllers, or programs that are in communication with one another may communicate directly or indirectly through one or more intermediaries.

During operation of the computing device, data may be received at the processor 202 from a pressure sensor, a temperature sensor, an optical sensor, and an accelerometer. As described herein, this data may originate at the intravenous device described in connection with FIG. 1 and be used to facilitate early detection of any patient deterioration or adverse infusion or drug reactions. The data provided by the pressure sensor, temperature sensor, optical sensor, and accelerometer may be used individually or in combination by the processor of the computing device in order to generate conclusions as to the early detection of patient deterioration and adverse infusion/drug reactions and provide instructions to the clinician as to best counteract any adverse effects the patient may be experiencing due to the care being provided.

Figure 3:
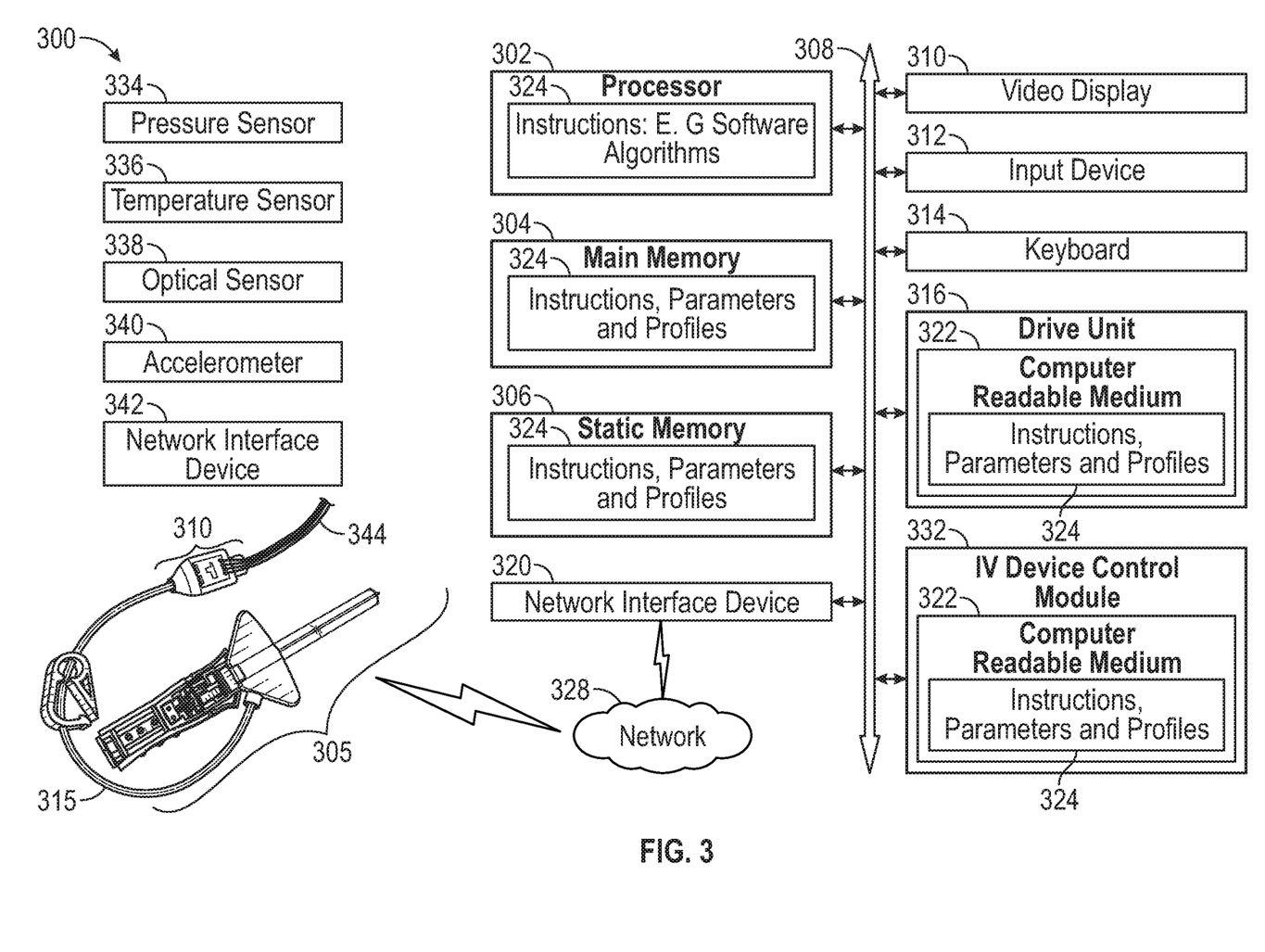
FIG. 3 is a block diagram of an intravenous system according to an embodiment of the present disclosure.

FIG. 3 is a block diagram of an intravenous therapy system 300 according to an embodiment of the present disclosure. In FIG. 3, a number of sensors of an intravenous device may be communicatively coupled to a processor of a computing device via a wireless connection over a network 328. As described herein, the sensors may include, among other types of sensors, a pressure sensor 334, a temperature sensor 336, an optical sensor 338, and an accelerometer 340. Each of these sensors 334, 336, 338, 340, may be formed on or operatively coupled to a PCB 310 of the intravenous device. Each of the sensors 334, 336, 338, 340 may be placed on the intravenous device such that the various biological characteristics related to a plurality of patient vitals may be detected. A network interface device 342 of the intravenous device may communicate data from the sensors 334, 336, 338, 340 over the network 328 using a network interface device 320 of the computing device, and to a processor that executes or operates the IV device control module 332 as described herein.

In some embodiments, one or more of the sensors 334, 336, 338, and 340 may be proximate or in contact with the fluidic path. In some embodiments, one or more of the sensors 334, 336, 338, and 340 may be disposed within the catheter 105 (see, for example, FIG. 1). In some embodiments, one or more of the sensors 334, 336, 338, and 340 may be disposed within an inner surface of the catheter 105 proximate an inner lumen of the catheter 105. In some embodiments, one or more of the sensors 334, 336, 338, and 340 may be disposed within the fluidic path at any suitable location. In some embodiments, one or more of the sensors 334, 336, 338, and 340 may include or correspond to the sensor 112 of FIG. 1.

During operation of the intravenous therapy system 300, a clinician may insert a needle of the intravenous device into a blood vessel of a patient. The intravenous device may fluidically couple the blood of the patient to each of the pressure sensor 334, temperature sensor 336, optical sensor 338, and accelerometer 340 via, in some embodiments, tubing 315 as described herein. Data from these sensors 334, 336, 338, 340 may be collected and sent to a processor 302. As described herein, the processor 302 may be formed within a computing device in an embodiment. In another embodiment, the processor 302 may be formed on a stabilization patch used to secure the intravenous device to the body of the patient. In this embodiment, a network interface device may establish a wireless connection with a computing device in order to provide information to a clinician related to the care of the patient. With the processor 302 located on the stabilization patch, the processing of the data may be accomplished prior to information being provided to, for example, a video display remote from either the stabilization patch or intravenous device.

The data received by the processor 302 may be saved in, for example, a patient care database that saves these patient vitals and other data descriptive of care provided to the patient. In an embodiment, the data received from the sensors 334, 336, 338, 340 may be compiled with other patient condition data such as blood tests present on the patient care database. This compilation of data may provide instructions or warnings to the clinician regarding prior treatments that may have adversely affected the patient. Additionally, the data received by the sensors 334, 336, 338, 340 and compiled with the patient care database may be further analyzed with other data such as fluid delivery data from any fluid delivery devices and medicament delivery confirmation systems with the intravenous device to confirm an infusion event, track patient responses, and/or provide suggestions to the clinician as to how to alter a treatment or therapy provided to the patient.

The video display 310 of the computing device may be used by a clinician to track the condition of the patient, detect changes in the condition of the patient which may indicate deterioration, and ultimately send out alarms to the clinician or other HCP. In an embodiment, the alarms or warnings may include instructions to the clinician regarding how to counteract any adverse reactions or deterioration of the patient's health that has occurred. When combined with information from any drug or therapy delivery devices, the vital data from the sensors 334, 336, 338, 340 may be further used to confirm the occurrence of therapeutic delivery and the patient response to treatment.

In an embodiment, the intravenous device may be communicatively coupled to the processor 302 via a number of electrical lines 344. The electrical lines 344 may send and received signals to and from the processor 302 as well as electrically couple each of the sensors 334, 336, 338, 340 to a power source (not shown) such as a battery.

The intravenous device described herein may be a single use device used for one patient in order to infuse one or more infusing fluids, such as normal saline solution, various medicaments, and total parenteral nutrition into the bloodstream of the patient or receive a blood sample. The intravenous device may, in some embodiments, be provided to the clinician as a kit that includes, at least, the intravenous device and the stabilization patch. In this embodiment, the kit may be used to communicate wirelessly with a computing device by engaging in, for example, a wireless device connection protocol that includes a Bluetooth connection, a Wi-Fi connection, and a mobile connection, among other types of wireless connections.

FIG. 4 is a flow diagram illustrating a method of operating an intravenous therapy system 420 according to an embodiment of the present disclosure. At panel 405, a patient 410 may be prepared to have the IV device of the intravenous therapy system 420 placed within a blood vessel.

At panel 415 the patient 410 has the IV device placed within the blood vessel. The IV device described herein, measures the patient's vitals continuously in between spot checks of the clinician. In panel 415 the infusion may have already proceeded and the clinician may have left the bedside of the patient 410 in order to allow the fusion to continue while engaging in other clinician-related tasks. Again, as described herein, the sensors 334, 336, 338, 340 may be continuously measuring a pulse rate, a body temperature, a respiratory rate, a blood/oxygen leave (SpO2), and venous oximetry. During this process, the intravenous device may monitor for any abnormal signs and trends continuously even when the clinician is away from the patient 410. In an embodiment, the intravenous device communicates with an infusion pump 425 and a display device 430.

At panel 435, the IV device 420 may be continuously monitoring for any infiltration, extravasation, and dislodgement of the IV device 420. If the patient 410 gets out of bed, for example, the IV device 420 may monitor for any falls that may occur. If a fall is detected by the accelerometer 340, the clinician may be notified at the display device 430.

At panel 440, the IV device 420 has detected an abnormal pulse rate. The IV device 420, via a processor, may send a message to the clinician at the display device 430 along with a trend graph associated with the pulse rate detected by the pressure sensor.

At panel 445, the clinician 450 is present at the display device 430 receiving the warning provided by the IV device 420. This may alert the clinician 450 to the cause to of the warning as well as any relevant patient data related to the warning. At panel 455, the clinician 450 may attend to the patient 410 by addressing the warnings that may or may not include adjustments to the infusion pump 425 and or IV device 420.

Figure 5:
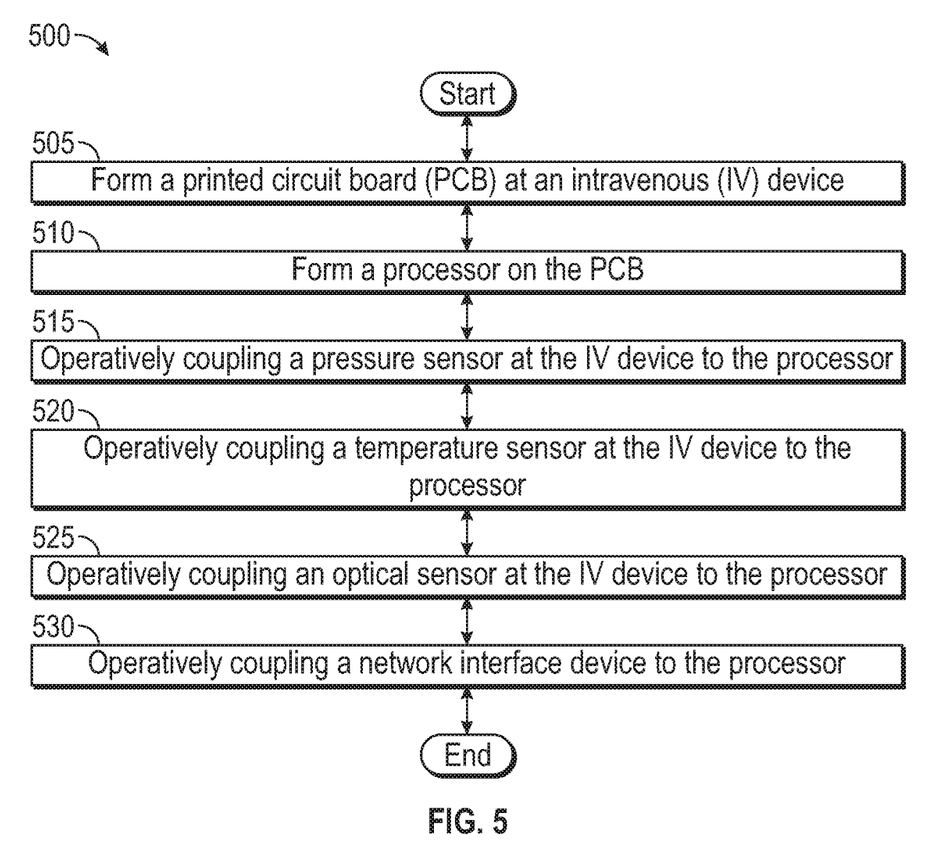
FIG. 5 is a flowchart illustrating a method of manufacturing an intravenous therapy system according to an embodiment of the present disclosure.

FIG. 5 is a flowchart illustrating a method 500 of manufacturing an intravenous therapy system according to an embodiment of the present disclosure. The method 500 may include forming a printed circuit board (PCB) at the intravenous (IV) device at block 505. As described herein, the IV device may include any number of other devices and sensors that may be used to determine certain vitals of the patient.

The method 500 may include, at block 510, forming a processor on the PCB. In an embodiment, the processor may be formed on a stabilization patch that is used to secure the IV device to the patient's body.

The method 500 may also include, at block 515, operatively coupling a pressure sensor at the IV device to the processor. In an embodiment, the pressure sensor may measure a pressure of fluids passed through the tubing, adaptor, connector, or other fluidic channel formed in the intravenous device. In an embodiment, the PCB may be placed such that the pressure sensor is also in fluidic communication with the tubing or other fluidic channel. In an embodiment, the pressure sensor may measure the pulse of the of the patient. In this embodiment, the pressure sensor may be placed along a fluidic path through which blood may pass during, for example, a blood drawing procedure.

The method 500 may also include, at block 520, operatively coupling a temperature sensor at the IV device to the processor. The temperature sensor may measure the temperature of the blood within the patient's body. The temperature sensor, in an embodiment, may be placed within the tubing of the intravenous device. In an embodiment, the temperature sensor may be placed on an outer surface of the tubing. In an embodiment, the temperature sensor may be in fluidic contact with venous blood such that the temperature of the blood within the patient's blood may be measured.

The method 500 may further include operatively coupling an optical sensor at the IV device to the processor, at block 525. In an embodiment, the optical sensor may be used to detect the pulse of the patient. In this embodiment, a light-emitting diode (LED) or other light source may be used according to the principles of plethysmography. As a change a volume of blood through an organ, such as the skin of the patient, may cause a change in light intensity through or reflected through the skin such that the optical sensor may detect such changes indicating a pulse. The results from the optical sensor indicating a pulse rate may be compared, in an embodiment, to a detected pulse rate detected by the pressure sensor described herein. This comparison may be conducted by the processor so as to determine an average of the pulse detected.

In an embodiment, the optical sensor may be placed within or near the tubing of the intravenous device. In an embodiment, the optical sensor may be placed at any location where a sample of the patient's blood may be optically accessed by the optical sensor in order to detect the oxygenation of patient's blood. In an embodiment, the optical sensor may form part of the stabilization patch described herein. In any of these embodiments, the optical sensor may be communicatively coupled to the processor in order to provide to the processor data descriptive of the pulse of the patient and/or the oxygenation of the patient's blood.

The method 500 may include, at block 530, operatively coupling a communication device to the processor. The communication device include a network interface device or another suitable communication device configured for input and output. The network interface device may provide connectivity to a network, e.g., a wide area network (WAN), a local area network (LAN), wireless local area network (WLAN), a wireless personal area network (WPAN), a wireless wide area network (WWAN), or other networks. Connectivity may be via wired or wireless connection. The network interface device may operate in accordance with any wireless data communication standards.

Again, it is understood that the embodiments of the present application may be combined. As an example, the embodiments of FIGS. 1-5 may be arranged to fit specific uses based on the type of action being conducted.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the disclosed embodiments.

The invention claimed is:

1. An intravenous therapy system comprising:
 an intravenous (IV) device, comprising:
  a needle;
  a catheter coaxially formed around the needle and extending from a catheter hub;
  a fluidic path fluidically coupled to a hollow formed through the needle and catheter;
  a printed circuit board (PCB), comprising a communication device configured to communicate with a processor; and
  a plurality of sensors operatively coupled to the PCB, wherein the plurality of sensors are within the catheter distal to the catheter hub and proximate the fluidic path to measure a biological characteristic related to a plurality of patient vitals; and
 a stabilization patch that is separate from the IV device and positioned overtop the IV device to secure the IV device to a patient's body, the processor and a network interface being integrated into the stabilization patch, wherein the processor is configured to use the network interface to establish a connection with the communication device of the PCB to receive sensor data generated by the plurality of sensors and to establish a connection with a computing device to relay the sensor data to the computing device.

2. The intravenous therapy system of claim 1, wherein the plurality of sensors comprises a pressure sensor fluidically coupled to a fluid path in the IV device to measure a pulse of the patient.

3. The intravenous therapy system of claim 2, wherein the processor or computing device is configured to perform a fast Fourier transform on the sensor data from the pressure sensor to detect a pressure trace.

4. The intravenous therapy system of claim 1, wherein the plurality of sensors comprises a temperature sensor to measure a temperature of blood within the patient's body.

5. The intravenous therapy system of claim 4, wherein the temperature sensor is operatively coupled to a fluidic path in the IV device used to house venous blood of the patient.

6. The intravenous therapy system of claim 1, wherein the plurality of sensors comprises an optical sensor to measure an oxygen level within blood of the patient's body.

7. The intravenous therapy system of claim 6, further comprising a pressure sensor to detect a pulse of the patient and wherein the optical sensor detects the pulse of the patient and compares the detected pulse rate with the detected pulse rate from the pressure sensor.

8. The intravenous therapy system of claim 1, wherein the plurality of sensors is formed within a microfluidic die operatively coupled to the PCB.

9. An intravenous (IV) therapy system, comprising:
 an IV device comprising:
  a needle;
  a catheter coaxially formed around the needle;
  a fluidic path fluidically coupled to a hollow formed through the needle and catheter;
  a printed circuit board (PCB), comprising a communication device configured to communicate with a processor;
  a plurality of sensors operatively coupled to the fluidic path to measure a biological characteristic related to a plurality of patient vitals, wherein at least one of the plurality of sensors is disposed within the fluidic path between the needle and the catheter; and
 a stabilization patch that is separate from the IV device and positioned overtop the IV device to secure the IV device to a patient's body, the processor and a network interface being integrated into the stabilization patch, wherein the processor is configured to use the network interface to establish a connection with the communication device of the PCB to receive sensor data generated by the plurality of sensors and to establish a connection with the computing device to relay the sensor data to the computing device.

10. The intravenous therapy system of claim 9, wherein the plurality of sensors comprises a pressure sensor fluidically coupled to a fluid path in the IV device to measure a pulse of the patient.

11. The intravenous therapy system of claim 9, wherein the plurality of sensors comprises a temperature sensor to measure a temperature of blood within the patient's body.

12. The intravenous therapy system of claim 9, wherein the plurality of sensors comprises an accelerometer to detect a rapid fall of the patient when the IV device is inserted into the patient's body.

13. A method for manufacturing an intravenous therapy system comprising:
 assembling an intravenous (IV) device, comprising:

a needle;

a catheter coaxially formed around the needle and extending from a catheter hub;

a fluidic path fluidically coupled to a hollow formed through the needle and catheter;

a printed circuit board (PCB), comprising a communication device configured to communicate with a processor; and a plurality of sensors operatively coupled to the PCB, wherein the plurality of sensors are within the catheter distal to the catheter hub and proximate the fluidic path to measure a biological characteristic related to a plurality of patient vitals; and assembling a stabilization patch that is separate from the IV device and positioned overtop the IV device to secure the IV device to a patient's body, the processor and a network interface being integrated into the stabilization patch, wherein the processor is configured to use the network interface to establish a connection with the communication device of the PCB to receive sensor data generated by the plurality of sensors and to establish a connection with the computing device to relay the sensor data to the computing device.

14. The method of claim 13, wherein the plurality of sensors comprises a pressure sensor fluidically coupled to a fluid path in the IV device to measure a pulse of the patient.

15. The method of claim 13, wherein the plurality of sensors comprises a temperature sensor to measure a temperature of blood within the patient's body.

16. The method of claim 13, wherein the plurality of sensors comprises an optical sensor to measure an oxygen level within blood of the patient's body.

17. The method of claim 13, wherein the plurality of sensors comprises an accelerometer.

18. The intravenous therapy system of claim 1, wherein the plurality of sensors comprises a pressure sensor, a temperature sensor, an optical sensor, and an accelerometer.

19. The intravenous therapy system of claim 18, wherein the plurality of sensors are in the form of a microfluidic chip.

20. The intravenous therapy system of claim 1, further comprising:

computer-readable media storing an IV device control module that is configured to receive the sensor data from the processor and to raise one or more alerts in response to processing the sensor data.

* * * * *